US006733760B1

(12) United States Patent
Wilkins et al.

(10) Patent No.: US 6,733,760 B1
(45) Date of Patent: May 11, 2004

(54) RECOMBINANT TOXIN A/TOXIN B VACCINE AGAINST CLOSTRIDIUM DIFFICILE

(75) Inventors: Tracy D. Wilkins, Riner, VA (US); David M. Lyerly, Radford, VA (US); J. Scott Moncrief, Christiansburg, VA (US); Limin Zheng, Blacksburg, VA (US); Carol Phelps, Floyd, VA (US)

(73) Assignee: Techlab, Inc., Blacksburg, VA (US)

( * ) Notice: Subject to any disclaimer, the term of this patent is extended or adjusted under 35 U.S.C. 154(b) by 0 days.

(21) Appl. No.: 09/545,773

(22) Filed: Apr. 10, 2000

Related U.S. Application Data

(60) Provisional application No. 60/190,111, filed on Mar. 20, 2000, provisional application No. 60/186,201, filed on Mar. 1, 2000, and provisional application No. 60/128,686, filed on Apr. 9, 1999.

(51) Int. Cl.[7] ......................... A61K 39/08; A61K 49/00; A61K 39/00; A61K 39/02
(52) U.S. Cl. ..................... 424/247.1; 424/9.1; 424/9.2; 424/184.1; 424/185.1; 424/192.1; 424/200.1; 424/234.1; 530/300; 530/350
(58) Field of Search ....................... 424/9.1, 9.2, 184.1, 424/185.1, 192.1, 200.1, 234.1, 247.1; 530/300, 350

(56) References Cited

U.S. PATENT DOCUMENTS

| | | |
|---|---|---|
| 4,530,833 A | 7/1985 | Wilkins et al. |
| 4,533,630 A | 8/1985 | Wilkins et al. |
| 4,863,852 A | 9/1989 | Wilkins et al. |
| 4,879,218 A | 11/1989 | Wilkins et al. |
| 5,098,826 A | 3/1992 | Wilkins et al. |
| 5,736,139 A | 4/1998 | Kink et al. |
| 5,919,463 A | 7/1999 | Thomas et al. |

FOREIGN PATENT DOCUMENTS

| | | |
|---|---|---|
| WO | WO 96/12802 | 5/1996 |
| WO | WO 97/02836 | 1/1997 |

OTHER PUBLICATIONS

Barroso et al., 1990, "Nucleotide Sequence of Clostridium Difficile Toxin B Gene" Nucl. Acids Res. 18:4004.

Dove et al., 1990, "Molecular Characterization of the Clostridium Difficile Toxin A Gene" Infect. Immun. 58:480–488.

Eichel–Streiber et al., 1992, "Clostridium Difficile Toxin A Carries a C–Terminal Repetitive Structure Homologous to the Carbohydrate Binding Region of Streptococcal Glycosyltransferases" Gene 96:107–113.

Faust et al., 1998, "The Enzymatic Domain of Clostridium Difficile Toxin A is Located within its N–Terminal Region" Biochem. Biophys. Res. Commun. 251:100–105.

Hofmann et al., 1997, "Localization of the Glucosyltransferase Activity of Clostridium Difficile Toxin B to the N–terminal Part of the Holotoxin" J. Biol. Chem. 272:11074–11078.

Just et al., 1995, "Glucosylation of Rho Proteins by Clostridium Difficile Toxin B"Nature 375:500–503.

Just et al., 1995, The Enterotoxin from Clostridium Difficile (ToxA) Monoglucosylates the Rho Proteins J. Biol. Chem. 270:13932–13939..

Krivan et al., 1986, "Cell Surface Binding Site for Clostridium difficile Enterotoxin: Evidence for a Glycoconjugate Containing the Sequence . . . " Infect. Immun. 53:573–581.

Lyerly et al., 1995 "Infections of the Gastrointestinal Tract" Chapter 58, pp. 867–891.

Lyerly et al., 1990, "Vaccination against Lethal Clostridium difficile Enterocolitis with a Nontoxic Recombinant Peptide of Toxin A" Current Microbiology 21:29–32.

Makoff et al., 1989, "Expression of Tetanus Toxin Fragment C in *E. Coli:* Its Purification and potential use as a Vaccine" Bio/Technology 7:1043–1046.

Makoff et al., 1989, "Expression of Tetanus Toxin Fragment C in *E coli:* High Level Expression by Removing Rare Codons" Nucleic Acids Res. 17:10191–10202.

Moncrief et al., 1997, "Positive Regulation of Clostridium difficile Toxins" Infect. Immun. 65:1105–1108.

Tucker et al., 1991, "Toxin A of Clostridium difficile Binds to the Human Carbohydrate Antigens I, X and Y" Infect. Immun. 59:73–78.

*Primary Examiner*—Rodney P Swartz
(74) *Attorney, Agent, or Firm*—Morrison & Foerster LLP

(57) ABSTRACT

The present invention relates to the field of medical immunology and further to pharmaceutical compositions, methods of making and methods of use of vaccines. More specifically this invention relates to recombinant proteins derived from the genes encoding *Clostridium difficile* toxin A and toxin B, and their use in an active vaccine against *C. difficile.*

9 Claims, 11 Drawing Sheets

Toxin A

Toxin B

Glucosyltransferase Domain

Active site
DXD motif

Binding Domain

Repeating units

Fig. 1

```
gatcctatag aatttaactt agtaactgga tggcaaacta tcaatggtaa
aaaatattat tttgatataa atactggagc agctttaact agttataaaa
ttattaatgg taaacacttt tattttaata atgatggtgt gatgcagttg
ggagtattta aaggacctga tggatttgaa tattttgcac ctgccaatac
tcaaaataat aacatagaag gtcaggctat agtttatcaa agtaaattct
taactttgaa tggcaaaaaa tattattttg ataataactc aaaagcagtc
actggatgga gaattattaa caatgagaaa tattacttta atcctaataa
tgctattgct gcagtcggat tgcaagtaat tgacaataat aagtattatt
tcaatcctga cactgctatc atctcaaaag gttggcagac tgttaatggt
agtagatact actttgatac tgataccgct attgccttta atggttataa
aactattgat ggtaaacact tttattttga tagtgattgt gtagtgaaaa
taggtgtgtt tagtacctct aatggatttg aatatttgc acctgctaat
acttataata ataacataga aggtcaggct atagtttatc aaagtaaatt
cttaactttg aatggtaaaa aatattactt tgataataac tcaaaagcag
ttaccggatg gcaaactatt gatagtaaaa aatattactt taatactaac
actgctgaag cagctactgg atggcaaact attgatggta aaaaatatta
ctttaatact aacactgctg aagcagctac tggatggcaa actattgatg
gtaaaaaata ttactttaat actaacactg ctatagcttc aactggttat
acaattatta atggtaaaca tttttatttt aatactgatg gtattatgca
gataggagtg tttaaggac ctaatggatt tgaatatttt gcacctgcta
atacggatgc taacaacata gaaggtcaag ctatacttta ccaaaatgaa
ttcttaactt gaatggtaa aaaatattac tttggtagtg actcaaaagc
agttactgga tggagaatta ttaacaataa gaaatattac tttaatccta
ataatgctat tgctgcaatt catctatgca ctataaataa tgacaagtat
tactttagtt atgatggaat tcttcaaaat ggatatatta ctattgaaag
aaataatttc tattttgatg ctaataatga atctaaaatg gtaacaggag
tatttaaagg acctaatgga tttgagtatt ttgcacctgc taatactcac
aataataaca tagaaggtca ggctatagtt taccagaaca aattcttaac
tttgaatggc aaaaaatatt attttgataa tgactcaaaa gcagttactg
gatggcaaac cattgatggt aaaaaatatt actttaatct taacactgct
gaagcagcta ctggatggca aactattgat ggtaaaaaat attactttaa
tcttaacact gctgaagcag ctactggatg gcaaactatt gatggtaaaa
aatattactt taatactaac actttcatag cctcaactgg ttatacaagt
attaatggta aacattttta ttttaatact gatggtatta tgcagatagg
agtgtttaaa ggacctaatg gatttgaata ctttgcacct gctaatacgg
atgctaacaa catagaaggt caagctatac tttaccaaaa taaattctta
actttgaatg gtaaaaaata ttactttggt agtgactcaa aagcagttac
cggactgcga actattgatg gtaaaaaata ttactttaat actaacactg
ctgttgcagt tactggatgg caaactatta atggtaaaaa atactacttt
aatactaaca cttctatagc ttcaactggt tatacaatta ttagtggtaa
acatttttat tttaatactg atggtattat gcagatagga gtgtttaaag
gacctgatgg atttgaatac tttgcacctg ctaatacaga tgctaacaat
atagaaggtc aagctatacg ttatcaaaat agatcctat atttacatga
caatatatat tattttggta ataattcaaa agcggctact ggttgggtaa
ctattgatgg taatagatat tacttcgagc ctaatacagc tatgggtgcg
aatggttata aaactattga taataaaaat tttacttta gaaatggttt
acctcagata ggagtgttta aagggtctaa tggatttgaa tactttgcac
ctgctaatac ggatgctaac aatatagaag gtcaagctat acgttatcaa
aatagattcc tacatttact tggaaaaata tattactttg gtaataattc
aaaagcagtt actggatggc aaactattaa tggtaaagta tattacttta
tgcctga (SEQ ID NO:1)
```

Fig. 2

```
DPIEFNLVTGWQTINGKKYYFDINTGAALTSYKIINGKHFY
FNNDGVMQLGVFKGPDGFEYFAPANTQNNNIEGQAIVYQSK
FLTLNGKKYYFDNNSKAVTGWRIINNEKYYFNPNNAIAAVG
LQVIDNNKYYFNPDTAIISKGWQTVNGSRYYFDTDTAIAFN
GYKTIDGKHFYFDSDCVVKIGVFSTSNGFEYFAPANTYNNN
IEGQAIVYQSKFLTLNGKKYYFDNNSKAVTGWQTIDSKKYY
FNTNTAEAATGWQTIDGKKYYFNTNTAEAATGWQTIDGKKY
YFNTNTAIASTGYTIINGKHFYFNTDGIMQIGVFKGPNGFE
YFAPANTDANNIEGQAILYQNEFLTLNGKKYYFGSDSKAVT
GWRIINNKKYYFNPNNAIAAIHLCTINNDKYYFSYDGILQN
GYITIERNNFYFDANNESKMVTGVFKGPNGFEYFAPANTHN
NNIEGQAIVYQNKFLTLNGKKYYFDNDSKAVTGWQTIDGKK
YYFNLNTAEAATGWQTIDGKKYYFNLNTAEAATGWQTIDGK
KYYFNTNTFIASTGYTSINGKHFYFNTDGIMQIGVFKGPNG
FEYFAPANTDANNIEGQAILYQNKFLTLNGKKYYFGSDSKA
VTGLRTIDGKKYYFNTNTAVAVTGWQTINGKKYYFNTNTSI
ASTGYTIISGKHFYFNTDGIMQIGVFKGPDGFEYFAPANTD
ANNIEGQAIRYQNRFLYLHDNIYYFGNNSKAATGWVTIDGN
RYYFEPNTAMGANGYKTIDNKNFYFRNGLPQIGVFKGSNGF
EYFAPANTDANNIEQAIRYQNRFLHLLGKIYYFGNNSKAVT
GGWQTINGKVYYFMPDTAMAAAGGLFEDGVIYFFGVDGVKA
PGIYG* (SEQ ID NO:2)
```

Fig. 3

```
gatctatcta tacgatatgt atggagtaat gatggtaatg attttattct tatgtcaact
agtgaagaaa ataaggtgtc acaagttaaa ataagattcg ttaatgtttt taaagataag
actttggcaa ataagctatc ttttaacttt agtgataaac aagatgtacc tgtaagtgaa
ataatcttat catttacacc ttcatattat gaggatggat tgattggcta tgatttgggt
ctagtttctt tatataatga gaaattttat attaataact ttggaatgat ggtatctgga
ttaatatata ttaatgattc attatattat tttaaaccac cagtaaataa tttgataact
ggatttgtga ctgtaggcga tgataaatac tactttaatc caattaatgg tggagctgct
tcaattggag agacaataat tgatgacaaa aattattatt tcaaccaaag tggagtgtta
caaacaggtg tatttagtac agaagatgga tttaaatatt ttgccccagc taatacactt
gatgaaaacc tagaaggaga agcaattgat tttactggaa aattaattat tgacgaaaat
atttattatt ttgatgataa ttatagagga gctgtagaat ggaaagaatt agatggtgaa
atgcactatt ttagcccaga aacaggtaaa gcttttaaag gtctaaatca aataggtgat
tataaatact atttcaattc tgatggagtt atgcaaaaag gatttgttag tataaatgat
aataaacact attttgatga ttctggtgtt atgaaagtag gttacactga aatagatggc
aagcatttct actttgctga aaacggagaa atgcaaatag gagtatttaa tacagaagat
ggatttaaat attttgctca tcataatgaa gatttaggaa atgaagaagg tgaagaaatc
tcatattctg gtatattaaa tttcaataat aaaatttact attttgatga ttcatttaca
gctgtagttg gatggaaaga tttagaggat ggttcaaagt attatttga tgaagataca
gcagaagcat atataggttt gtcattaata aatgatggtc aatatattt taatgatgat
ggaattatgc aagttggatt tgtcactata aatgataaag tcttctactt ctctgactct
ggaattatag aatctggagt acaaaacata gatgacaatt atttctatat agatgataat
ggtatagttc aaattggtgt atttgatact tcagatggat ataaatattt tgcacctgct
aatactgtaa atgataatat ttacggacaa gcagttgaat atagtggttt agttagagtt
ggggaagatg tatattattt tggagaaaca tatacaattg agactggatg gatatatgat
atggaaaatg aaagtgataa atattatttc aatccagaaa ctaaaaaagc atgcaaaggt
attaatttaa ttgatgatat aaaatattat tttgatgaga agggcataat gagaacgggt
cttatatcat ttgaaaataa taattattac tttaatgaga atggtgaaat gcaatccggt
tatataaata tagaagataa gatgttctat tttggtgaag atggtgtcat gcagattgga
gtatttaata caccagatgg atttaaatac tttgcacatc aaaatacttt ggatgagaat
tttgagggag aatcaataaa ctatactggt tggttagatt tagatgaaaa gagatattat
tttacagatg aatatattgc agcaactggt tcagttatta ttgatggtga ggagtattat
tttgatcctg atacagctca attagtgatt agtgaataga taaaaatatg ttaaatatat
cctcttatac ttaaatatat aaaaataaac aaaatgatac actacataaa gtgttctatc
taatatgaag atttaccaat aaaaaggtgg actatgatga atgcacagta gttcacccttt
ttatattact aatggtaaca aaatattttt ttatataaac ctaggaggcg tt// (SEQ ID NO:3)
```

Fig. 6

```
DLSIRYVWSNDGNDFILMSTSEENKVSQVKIRFVNVFKDKTLANKLSFNF
SDKQDVPVSEIILSFTPSYYEDGLIGYDLGLVSLYNEKFYINNFGMMVSG
LIYINDSLYYFKPPVNNLITGFVTVGDDKYYFNPINGGAASIGETIIDDK
NYYFNQSGVLQTGVFSTEDGFKYFAPANTLDENLEGEAIDFTGKLIIDEN
IYFDDNYRGAVEWKELDGEMHYFSPETGKAFKGLNQIGDYKYYFNSDGVM
QKGFVSINDNKHYFDDSGVMKVGYTEIDGKHFYFAENGEMQIGVFNTEDG
FKYFAHHNEDLGNEEGEEISYSGILNFNNKIYYFDDSFTAVVGWKDLEDG
SKYYFDEDTAEAYIGLSLINDGQYYFNDDGIMQVGFVTINDKVFYFSDSG
IIESGVQNIDDNYFYIDDNGIVQIGVFDTSDGYKYFAPANTVNDNIYGQA
VEYSGLVRVGEDVYYFGETYTIETGWIYDMENESDKYYFNPETKKACKGI
NLIDDIKYYFDEKGIMRTCLISFENNNYYFNENGEMQFGYINIEDKMFYF
GEDGVMQIGVFNTPDGFKYFAHQNTLDENFEGESINYTGWLDLDEKRYYF
TDEYIAATGSVIIDGEEYYFDPDTAQLVISE (SEQ ID NO:4)
```

*C. difficile* toxin B

*E. coli* rBRU

Figure 10

SEQUENCE LISTING

<160> NUMBER OF SEQ ID NOS: 4

<210> SEQ ID NO 1
<211> LENGTH: 2507
<212> TYPE: DNA
<213> ORGANISM: Clostridium difficile

<400> SEQUENCE: 1

```
gatcctatag aatttaactt agtaactgga tggcaaacta tcaatggtaa aaaatattat        60
tttgatataa atactggagc agctttaact agttataaaa ttattaatgg taaacacttt       120
```

-continued

```
tattttaata atgatggtgt gatgcagttg ggagtattta aaggacctga tggatttgaa      180
tattttgcac ctgccaatac tcaaaataat aacatagaag gtcaggctat agtttatcaa      240
agtaaattct taactttgaa tggcaaaaaa tattattttg ataataactc aaaagcagtc      300
actggatgga gaattattaa caatgagaaa tattacttta atcctaataa tgctattgct      360
gcagtcggat tgcaagtaat tgacaataat aagtattatt tcaatcctga cactgctatc      420
atctcaaaag gttggcagac tgttaatggt agtagatact actttgatac tgataccgct      480 attgcccttta atggttataa aactattgat ggtaaaacact tttattttga tagtgattgt      540
gtagtgaaaa taggtgtgtt tagtacctct aatggatttg aatattttgc acctgctaat      600
acttataata ataacataga aggtcaggct atagtttatc aaagtaaatt cttaactttg      660
aatggtaaaa aatattactt tgataataac tcaaaagcag ttaccggatg gcaaactatt      720
gatagtaaaa aatattactt taatactaac actgctgaag cagctactgg atggcaaact      780
attgatggta aaaaatatta ctttaatact aacactgctg aagcagctac tggatggcaa      840
actattgatg gtaaaaaata ttactttaat actaacactg ctatagcttc aactggttat      900
acaattatta atggtaaaca ttttattttt aatactgatg gtattatgca gataggagtg      960
tttaaaggac ctaatggatt tgaatatttt gcacctgcta atacggatgc taacaacata     1020
gaaggtcaag ctatacttta ccaaaatgaa ttcttaactt tgaatggtaa aaaatattac     1080
tttggtagtg actcaaaagc agttactgga tggagaatta ttaacaataa gaaatattac     1140
tttaatccta ataatgctat tgctgcaatt catctatgca ctataaataa tgacaagtat     1200
tactttagtt atgatggaat tcttcaaaat ggatatatta ctattgaaag aaataatttc     1260
tattttgatg ctaataatga atctaaaatg gtaacaggag tatttaaagg acctaatgga     1320
tttgagtatt ttgcacctgc taatactcac aataataaca tagaaggtca ggctatagtt     1380
taccagaaca aattcttaac tttgaatggc aaaaaatatt attttgataa tgactcaaaa     1440
gcagttactg gatggcaaac cattgatggt aaaaaatatt actttaatct taacactgct     1500
gaagcagcta ctggatggca aactattgat ggtaaaaaat attactttaa tcttaacact     1560
gctgaagcag ctactggatg gcaaactatt gatggtaaaa aatattactt taatactaac     1620
actttcatag cctcaactgg ttatacaagt attaatggta acatttttta ttttaatact     1680
gatggtatta tgcagatagg agtgtttaaa ggacctaatg gatttgaata ctttgcacct     1740
gctaatacgg atgctaacaa catagaaggt caagctatac tttaccaaaa taattcttaa     1800
actttgaatg gtaaaaaata ttactttggt agtgactcaa aagcagttac cggactgcga     1860
actattgatg gtaaaaaata ttactttaat actaacactg ctgttgcagt tactggatgg     1920
caaactatta atggtaaaaa atactacttt aatactaaca cttctatagc ttcaactggt     1980
tatacaatta ttagtggtaa acatttttat tttaatactg atggtattat gcagatagga     2040
gtgtttaaag gacctgatgg atttgaatac tttgcacctg ctaatacaga tgctaacaat     2100
atagaaggtc aagctatacg ttatcaaaat agattcctat atttacatga caatatatat     2160
tattttggta ataattcaaa agcggctact ggttgggtaa ctattgatgg taatagatat     2220
tacttcgagc ctaatacagc tatgggtgcg aatggttata aaactattga taataaaaat     2280
ttttacttta gaaatggttt acctcagata ggagtgttta aagggtctaa tggatttgaa     2340
tactttgcac ctgctaatac ggatgctaac aatatagaag gtcaagctat acgttatcaa     2400
aatagattcc tacattact tggaaaaata tattactttg gtaataattc aaaagcagtt     2460
actggatggc aaactattaa tggtaaagta tattacttta tgcctga                   2507
```

```
<210> SEQ ID NO 2
<211> LENGTH: 866
<212> TYPE: PRT
<213> ORGANISM: Clostridium difficile

<400> SEQUENCE: 2

Asp Pro Ile Glu Phe Asn Leu Val Thr Gly Trp Gln Thr Ile Asn Gly
 1               5                  10                  15

Lys Lys Tyr Tyr Phe Asp Ile Asn Thr Gly Ala Ala Leu Thr Ser Tyr
             20                  25                  30

Lys Ile Ile Asn Gly Lys His Phe Tyr Phe Asn Asn Asp Gly Val Met
         35                  40                  45

Gln Leu Gly Val Phe Lys Gly Pro Asp Gly Phe Glu Tyr Phe Ala Pro
     50                  55                  60

Ala Asn Thr Gln Asn Asn Asn Ile Glu Gly Gln Ala Ile Val Tyr Gln
 65                  70                  75                  80

Ser Lys Phe Leu Thr Leu Asn Gly Lys Lys Tyr Tyr Phe Asp Asn Asn
                 85                  90                  95

Ser Lys Ala Val Thr Gly Trp Arg Ile Ile Asn Asn Glu Lys Tyr Tyr
            100                 105                 110

Phe Asn Pro Asn Asn Ala Ile Ala Ala Val Gly Leu Gln Val Ile Asp
        115                 120                 125

Asn Asn Lys Tyr Tyr Phe Asn Pro Asp Thr Ala Ile Ile Ser Lys Gly
    130                 135                 140

Trp Gln Thr Val Asn Gly Ser Arg Tyr Tyr Phe Asp Thr Asp Thr Ala
145                 150                 155                 160

Ile Ala Phe Asn Gly Tyr Lys Thr Ile Asp Gly Lys His Phe Tyr Phe
                165                 170                 175

Asp Ser Asp Cys Val Val Lys Ile Gly Val Phe Ser Thr Ser Asn Gly
            180                 185                 190

Phe Glu Tyr Phe Ala Pro Ala Asn Thr Tyr Asn Asn Asn Ile Glu Gly
        195                 200                 205

Gln Ala Ile Val Tyr Gln Ser Lys Phe Leu Thr Leu Asn Gly Lys Lys
    210                 215                 220

Tyr Tyr Phe Asp Asn Asn Ser Lys Ala Val Thr Gly Trp Gln Thr Ile
225                 230                 235                 240

Asp Ser Lys Lys Tyr Tyr Phe Asn Thr Asn Thr Ala Glu Ala Ala Thr
                245                 250                 255

Gly Trp Gln Thr Ile Asp Gly Lys Lys Tyr Tyr Phe Asn Thr Asn Thr
            260                 265                 270

Ala Glu Ala Ala Thr Gly Trp Gln Thr Ile Asp Gly Lys Lys Tyr Tyr
        275                 280                 285

Phe Asn Thr Asn Thr Ala Ile Ala Ser Thr Gly Tyr Thr Ile Ile Asn
    290                 295                 300

Gly Lys His Phe Tyr Phe Asn Thr Asp Gly Ile Met Gln Ile Gly Val
305                 310                 315                 320

Phe Lys Gly Pro Asn Gly Phe Glu Tyr Phe Ala Pro Ala Asn Thr Asp
                325                 330                 335

Ala Asn Asn Ile Glu Gly Gln Ala Ile Leu Tyr Gln Asn Glu Phe Leu
            340                 345                 350

Thr Leu Asn Gly Lys Lys Tyr Tyr Phe Gly Ser Asp Ser Lys Ala Val
        355                 360                 365

Thr Gly Trp Arg Ile Ile Asn Asn Lys Lys Tyr Tyr Phe Asn Pro Asn
```

```
              370                 375                 380
Asn Ala Ile Ala Ala Ile His Leu Cys Thr Ile Asn Asn Asp Lys Tyr
385                 390                 395                 400
Tyr Phe Ser Tyr Asp Gly Ile Leu Gln Asn Gly Tyr Ile Thr Ile Glu
                405                 410                 415
Arg Asn Asn Phe Tyr Phe Asp Ala Asn Asn Glu Ser Lys Met Val Thr
                420                 425                 430
Gly Val Phe Lys Gly Pro Asn Gly Phe Glu Tyr Phe Ala Pro Ala Asn
                435                 440                 445
Thr His Asn Asn Asn Ile Glu Gly Gln Ala Ile Val Tyr Gln Asn Lys
                450                 455                 460
Phe Leu Thr Leu Asn Gly Lys Lys Tyr Tyr Phe Asp Asn Asp Ser Lys
465                 470                 475                 480
Ala Val Thr Gly Trp Gln Thr Ile Asp Gly Lys Lys Tyr Tyr Phe Asn
                485                 490                 495
Leu Asn Thr Ala Glu Ala Ala Thr Gly Trp Gln Thr Ile Asp Gly Lys
                500                 505                 510
Lys Tyr Tyr Phe Asn Leu Asn Thr Ala Glu Ala Ala Thr Gly Trp Gln
                515                 520                 525
Thr Ile Asp Gly Lys Lys Tyr Tyr Phe Asn Thr Asn Thr Phe Ile Ala
                530                 535                 540
Ser Thr Gly Tyr Thr Ser Ile Asn Gly Lys His Phe Tyr Phe Asn Thr
545                 550                 555                 560
Asp Gly Ile Met Gln Ile Gly Val Phe Lys Gly Pro Asn Gly Phe Glu
                565                 570                 575
Tyr Phe Ala Pro Ala Asn Thr Asp Ala Asn Asn Ile Glu Gly Gln Ala
                580                 585                 590
Ile Leu Tyr Gln Asn Lys Phe Leu Thr Leu Asn Gly Lys Lys Tyr Tyr
                595                 600                 605
Phe Gly Ser Asp Ser Lys Ala Val Thr Gly Leu Arg Thr Ile Asp Gly
                610                 615                 620
Lys Lys Tyr Tyr Phe Asn Thr Asn Thr Ala Val Ala Val Thr Gly Trp
625                 630                 635                 640
Gln Thr Ile Asn Gly Lys Lys Tyr Tyr Phe Asn Thr Asn Thr Ser Ile
                645                 650                 655
Ala Ser Thr Gly Tyr Thr Ile Ile Ser Gly Lys His Phe Tyr Phe Asn
                660                 665                 670
Thr Asp Gly Ile Met Gln Ile Gly Val Phe Lys Gly Pro Asp Gly Phe
                675                 680                 685
Glu Tyr Phe Ala Pro Ala Asn Thr Asp Ala Asn Asn Ile Glu Gly Gln
                690                 695                 700
Ala Ile Arg Tyr Gln Asn Arg Phe Leu Tyr Leu His Asp Asn Ile Tyr
705                 710                 715                 720
Tyr Phe Gly Asn Asn Ser Lys Ala Ala Thr Gly Trp Val Thr Ile Asp
                725                 730                 735
Gly Asn Arg Tyr Tyr Phe Glu Pro Asn Thr Ala Met Gly Ala Asn Gly
                740                 745                 750
Tyr Lys Thr Ile Asp Asn Lys Asn Phe Tyr Phe Arg Asn Gly Leu Pro
                755                 760                 765
Gln Ile Gly Val Phe Lys Gly Ser Asn Gly Phe Glu Tyr Phe Ala Pro
                770                 775                 780
Ala Asn Thr Asp Ala Asn Asn Ile Glu Gln Ala Ile Arg Tyr Gln Asn
785                 790                 795                 800
```

Arg Phe Leu His Leu Leu Gly Lys Ile Tyr Tyr Phe Gly Asn Asn Ser
            805                 810                 815

Lys Ala Val Thr Gly Gly Trp Gln Thr Ile Asn Gly Lys Val Tyr Tyr
            820                 825                 830

Phe Met Pro Asp Thr Ala Met Ala Ala Gly Gly Leu Phe Glu Asp
            835                 840                 845

Gly Val Ile Tyr Phe Phe Gly Val Asp Gly Val Lys Ala Pro Gly Ile
            850                 855                 860

Tyr Gly
865

<210> SEQ ID NO 3
<211> LENGTH: 2092
<212> TYPE: DNA
<213> ORGANISM: Clostridium difficile

<400> SEQUENCE: 3

| | | | | | |
|---|---|---|---|---|---|
| gatctatcta | tacgatatgt | atggagtaat | gatggtaatg | attttattct | tatgtcaact | 60 |
| agtgaagaaa | ataaggtgtc | acaagttaaa | ataagattcg | ttaatgtttt | taaagataag | 120 |
| actttggcaa | ataagctatc | ttttaacttt | agtgataaac | aagatgtacc | tgtaagtgaa | 180 |
| ataatcttat | catttacacc | ttcatattat | gaggatggat | tgattggcta | tgatttgggt | 240 |
| ctagtttctt | tatataatga | gaaattttat | attaataact | ttggaatgat | ggtatctgga | 300 |
| ttaatatata | ttaatgattc | attatattat | tttaaaccac | cagtaaataa | tttgataact | 360 |
| ggatttgtga | ctgtaggcga | tgataaatac | tactttaatc | caattaatgg | tggagctgct | 420 |
| tcaattggag | agacaataat | tgatgacaaa | aattattatt | caaccaaag | tggagtgtta | 480 |
| caaacaggtg | tatttagtac | agaagatgga | tttaaatatt | ttgccccagc | taatacactt | 540 |
| gatgaaaacc | tagaaggaga | agcaattgat | tttactggaa | aattaattat | tgacgaaaat | 600 |
| atttattatt | ttgatgataa | ttatagagga | gctgtagaat | ggaaagaatt | agatggtgaa | 660 |
| atgcactatt | ttagcccaga | aacaggtaaa | gcttttaaag | gtctaaatca | aataggtgat | 720 |
| tataaatact | atttcaattc | tgatggagtt | atgcaaaaag | gatttgttag | tataaatgat | 780 |
| aataaacact | attttgatga | ttctggtgtt | atgaaagtag | gttacactga | aatagatggc | 840 |
| aagcatttct | actttgctga | aaacggagaa | atgcaaatag | gagtatttaa | tacagaagat | 900 |
| ggatttaaat | attttgctca | tcataatgaa | gatttaggaa | atgaagaagg | tgaagaaatc | 960 |
| tcatattctg | gtatattaaa | tttcaataat | aaaatttact | attttgatga | ttcatttaca | 1020 |
| gctgtagttg | gatggaaaga | tttagaggat | ggttcaaagt | attattttga | tgaagataca | 1080 |
| gcagaagcat | ataggtttt | gtcattaata | aatgatggtc | aatattattt | taatgatgat | 1140 |
| ggaattatgc | aagttggatt | tgtcactata | aatgataaag | tcttctactt | ctctgactct | 1200 |
| ggaattatag | aatctggagt | acaaaacata | gatgacaatt | atttctatat | agatgataat | 1260 |
| ggtatagttc | aaattggtgt | atttgatact | tcagatggat | ataaatattt | tgcacctgct | 1320 |
| aatactgtaa | atgataatat | ttacggacaa | gcagttgaat | atagtggttt | agttagagtt | 1380 |
| ggggaagatg | tatattattt | tggagaaaca | tatacaattg | agactggatg | gatatatgat | 1440 |
| atggaaaatg | aaagtgataa | atattatttc | aatccagaaa | ctaaaaagc | atgcaaaggt | 1500 |
| attaatttaa | ttgatgatat | aaaatattat | tttgatgaga | agggcataat | gagaacgggt | 1560 |
| cttatatcat | ttgaaaataa | taattattac | tttaatgaga | atggtgaaat | gcaatttggt | 1620 |
| tatataaata | tagaagataa | gatgttctat | tttggtgaag | atggtgtcat | gcagattgga | 1680 |

-continued

```
gtatttaata caccagatgg atttaaatac tttgcacatc aaaatacttt ggatgagaat    1740
tttgagggag aatcaataaa ctatactggt tggttagatt tagatgaaaa gagatattat    1800
tttacagatg aatatattgc agcaactggt tcagttatta ttgatggtga ggagtattat    1860
tttgatcctg atacagctca attagtgatt agtgaataga taaaaatatg ttaaatatat    1920
cctcttatac ttaaatatat aaaaataaac aaaatgatac actacataaa gtgttctatc    1980
taatatgaag atttaccaat aaaaggtgg actatgatga atgcacagta gttcaccttt     2040
ttatattact aatggtaaca aaatattttt ttatataaac ctaggaggcg tt            2092
```

<210> SEQ ID NO 4
<211> LENGTH: 631
<212> TYPE: PRT
<213> ORGANISM: Clostridium difficile

<400> SEQUENCE: 4

```
Asp Leu Ser Ile Arg Tyr Val Trp Ser Asn Asp Gly Asn Asp Phe Ile
 1               5                  10                  15

Leu Met Ser Thr Ser Glu Glu Asn Lys Val Ser Gln Val Lys Ile Arg
             20                  25                  30

Phe Val Asn Val Phe Lys Asp Lys Thr Leu Ala Asn Lys Leu Ser Phe
         35                  40                  45

Asn Phe Ser Asp Lys Gln Asp Val Pro Val Ser Glu Ile Ile Leu Ser
     50                  55                  60

Phe Thr Pro Ser Tyr Tyr Glu Asp Gly Leu Ile Gly Tyr Asp Leu Gly
 65                  70                  75                  80

Leu Val Ser Leu Tyr Asn Glu Lys Phe Tyr Ile Asn Asn Phe Gly Met
                 85                  90                  95

Met Val Ser Gly Leu Ile Tyr Ile Asn Asp Ser Leu Tyr Tyr Phe Lys
            100                 105                 110

Pro Pro Val Asn Asn Leu Ile Thr Gly Phe Val Thr Val Gly Asp Asp
        115                 120                 125

Lys Tyr Tyr Phe Asn Pro Ile Asn Gly Gly Ala Ala Ser Ile Gly Glu
    130                 135                 140

Thr Ile Ile Asp Asp Lys Asn Tyr Tyr Phe Asn Gln Ser Gly Val Leu
145                 150                 155                 160

Gln Thr Gly Val Phe Ser Thr Glu Asp Gly Phe Lys Tyr Phe Ala Pro
                165                 170                 175

Ala Asn Thr Leu Asp Glu Asn Leu Glu Gly Glu Ala Ile Asp Phe Thr
            180                 185                 190

Gly Lys Leu Ile Ile Asp Glu Asn Ile Tyr Phe Asp Asp Asn Tyr Arg
        195                 200                 205

Gly Ala Val Glu Trp Lys Glu Leu Asp Gly Glu Met His Tyr Phe Ser
    210                 215                 220

Pro Glu Thr Gly Lys Ala Phe Lys Gly Leu Asn Gln Ile Gly Asp Tyr
225                 230                 235                 240

Lys Tyr Tyr Phe Asn Ser Asp Gly Val Met Gln Lys Gly Phe Val Ser
                245                 250                 255

Ile Asn Asp Asn Lys His Tyr Phe Asp Asp Ser Gly Val Met Lys Val
            260                 265                 270

Gly Tyr Thr Glu Ile Asp Gly Lys His Phe Tyr Phe Ala Glu Asn Gly
        275                 280                 285

Glu Met Gln Ile Gly Val Phe Asn Thr Glu Asp Gly Phe Lys Tyr Phe
    290                 295                 300
```

-continued

```
Ala His His Asn Glu Asp Leu Gly Asn Glu Glu Gly Glu Glu Ile Ser
305                 310                 315                 320

Tyr Ser Gly Ile Leu Asn Phe Asn Asn Lys Ile Tyr Tyr Phe Asp Asp
                325                 330                 335

Ser Phe Thr Ala Val Val Gly Trp Lys Asp Leu Glu Asp Gly Ser Lys
            340                 345                 350

Tyr Tyr Phe Asp Glu Asp Thr Ala Glu Ala Tyr Ile Gly Leu Ser Leu
        355                 360                 365

Ile Asn Asp Gly Gln Tyr Tyr Phe Asn Asp Asp Gly Ile Met Gln Val
    370                 375                 380

Gly Phe Val Thr Ile Asn Asp Lys Val Phe Tyr Phe Ser Asp Ser Gly
385                 390                 395                 400

Ile Ile Glu Ser Gly Val Gln Asn Ile Asp Asp Asn Tyr Phe Tyr Ile
            405                 410                 415

Asp Asp Asn Gly Ile Val Gln Ile Gly Val Phe Asp Thr Ser Asp Gly
            420                 425                 430

Tyr Lys Tyr Phe Ala Pro Ala Asn Thr Val Asn Asp Asn Ile Tyr Gly
        435                 440                 445

Gln Ala Val Glu Tyr Ser Gly Leu Val Arg Val Gly Glu Asp Val Tyr
    450                 455                 460

Tyr Phe Gly Glu Thr Tyr Thr Ile Glu Thr Gly Trp Ile Tyr Asp Met
465                 470                 475                 480

Glu Asn Glu Ser Asp Lys Tyr Tyr Phe Asn Pro Glu Thr Lys Lys Ala
            485                 490                 495

Cys Lys Gly Ile Asn Leu Ile Asp Asp Ile Lys Tyr Tyr Phe Asp Glu
            500                 505                 510

Lys Gly Ile Met Arg Thr Gly Leu Ile Ser Phe Glu Asn Asn Asn Tyr
        515                 520                 525

Tyr Phe Asn Glu Asn Gly Glu Met Gln Phe Gly Tyr Ile Asn Ile Glu
    530                 535                 540

Asp Lys Met Phe Tyr Phe Gly Glu Asp Gly Val Met Gln Ile Gly Val
545                 550                 555                 560

Phe Asn Thr Pro Asp Gly Phe Lys Tyr Phe Ala His Gln Asn Thr Leu
            565                 570                 575

Asp Glu Asn Phe Glu Gly Glu Ser Ile Asn Tyr Thr Gly Trp Leu Asp
            580                 585                 590

Leu Asp Glu Lys Arg Tyr Tyr Phe Thr Asp Glu Tyr Ile Ala Ala Thr
        595                 600                 605

Gly Ser Val Ile Ile Asp Gly Glu Glu Tyr Tyr Phe Asp Pro Asp Thr
    610                 615                 620

Ala Gln Leu Val Ile Ser Glu
625                 630
```

RECOMBINANT TOXIN A/TOXIN B VACCINE AGAINST *CLOSTRIDIUM DIFFICILE*

This application claims priority under 35 U.S.C § 119(e) of provisional applications Ser. No. 60/190,111 filed Mar. 20, 2000; Ser. No. 60/186,201 filed Mar. 1, 2000; and 60/128,686 filed Apr. 9, 1999. The content of these applications are incorporated herein by reference.

TECHNICAL FIELD OF INVENTION

The present invention relates to the field of medical immunology and further to pharmaceutical compositions, methods of making and methods of use of vaccines. More specifically this invention relates to recombinant proteins derived from the genes encoding *Clostridium difficile* toxin A and toxin B, and their use in an active vaccine against *C. difficile*.

BACKGROUND OF THE INVENTION

*Clostridium difficile*, a Gram positive anaerobic spore-forming bacillus is an etiologic agent of antibiotic associated diarrhea (AAD) and colitis (AAC). The symptoms of the disease range from mild diarrhea to fulminant and life-threatening pseudomembranous colitis (PMC). Antibiotic therapy can disrupt the normal intestinal microflora. Destruction of the normal flora results in a condition in which *C. difficile* can spores of *C. difficile* can germinate and the organism can grow and produce disease causing toxins. *C. difficile* causes about 25% of antibiotic-associated diarrheas, however, it is almost always the causative agent of PMC (Lyerly, D. M. and T. D. Wilkins, in *Infections of the Gastrointestinal Tract*, Chapter 58, pages 867–891, (Raven Press, Ltd, New York 1995)). Additionally, *C. difficile* is frequently identified as a causative agent of nosocomial infectious diarrheas, particularly in older or immuno-compromised patients (U.S. Pat. No. 4,863,852 (Wilkins et al.) (1989)).

Disease caused by *C. difficile* is due to two enteric toxins A and B produced by toxigenic strains (U.S. Pat. No. 5,098,826 (Wilkins et al.) (1992)). Toxin A is an enterotoxin with minimal cytotoxic activity, whereas toxin B is a potent cytotoxin but has limited enterotoxic activity. The extensive damage to the intestinal mucosa is attributable to the action of toxin A, however, toxins A and B act synergistically in the intestine.

The genetic sequences encoding both toxigenic proteins A and B, the largest known bacterial toxins, with molecular weights of 308,000 and 269,000, respectively, have been elucidated (Moncrief et al., *Infect. Immun.* 65:1105–1108 (1997); Barroso et al., *Nucl. Acids Res.* 18:4004 (1990); Dove et al. *Infect. Immun.* 58:480–488 (1990)). Because of the degree of similarity when conserved substitutions are considered, these toxins are thought to have arisen from gene duplication. The proteins share a number of similar structural features with one another. For example, both proteins possess a putative nucleotide binding site, a central hydrophobic region, four conserved cysteines and a long series of repeating units at their carboxyl ends. The repeating units of toxin A, particularly, are immunodominant and are responsible for binding to type 2 core carbohydrate antigens on the surface of the intestinal epithelium (Krivan et al., *Infect. Immun.* 53:573–581 (1986); Tucker, K. and T. D. Wilkins, *Infect. Immun.* 59:73–78 (1991)).

The toxins share a similar molecular mechanism of action involving the covalent modification of Rho proteins. Rho proteins are small molecular weight effector proteins that have a number of cellular functions including maintaining the organization of the cytoskeleton. The covalent modification of Rho proteins is due to glucosyltransferase activity of the toxins. A glucose moiety is added to Rho using UDP-glucose as a co-substrate (Just et al. *Nature* 375:500–503 (1995), Just et al. *J Biol. Chem* 270:13932–13939 (1995)). The glucosyltransferase activity has been localized to approximately the initial 25% of the amino acid sequence of each of these toxins (Hofmann et al. *J Biol. Chem.* 272:11074–11078 (1997), Faust and Song, *Biochem. Biophys. Res. Commun.* 251:100–105 (1998)) leaving a large portion of the toxins, including the repeating units, that do not participate in the enzymatic activity responsible for cytotoxicity.

The toxin A protein comprises 31 contiguous repeating units (rARU) and may contain multiple T cell epitopes (Dove et al. *Infect. Immun.* 58:480–488 (1990). The repeating units are defined as class I repeats and class II. rARU may be uniquely suited for use in inducing T cell-dependent response to an antigen. The sequence of each unit is similar but not identical. These features along with its usefulness in eliciting toxin A neutralizing antibodies make rARU a novel candidate as a carrier protein.

The toxin B repeating units have similar features to those of rARU. Like rARU, the recombinant toxin B repeating units (rBRU) are relatively large (~70 kDa) and are composed of contiguous repeats of similar amino acid sequences (Barroso et al. *Nucleic Acids Res.* 18:4004 (1990); Eichel-Streiber et al. *Gene* 96:107–113 (1992)). Less is known about this portion of toxin B than the binding domain of toxin A.

Thomas et al (U.S. Pat. No. 5,919,463 (1999)) disclose *C. difficile* toxin A or toxin B or certain fragments thereof as mucosal adjuvants intranasally administered to stimulate an immune response to an antigen (e.g., Helicobacter pylori urease, ovalbumin (OVA), or keyhole limpet hemocyanin (KLH)). However, Thomas does not teach the use of such adjuvant for protection against strains of *C. difficile*. Lyerly et al. *Current Microbiology* 21:29–32 (1990) considered at a smaller recombinant fragment from the toxin A repeats in hamster protection assays. However, these data suggest at best only a very weak or partial protection from strains of *C. difficile*, whereas the present invention demonstrates the use of *C. difficile* toxin repeating units that provide a clear immunogenic response and at higher levels, which afford protection against *C. difficile*.

Even were one to consider rARU and rBRU as candidate proteins for conjugate vaccines, the production of such proteins presents certain challenges. There are methods for the production of toxin A and antibodies elicited thereto (U.S. Pat. No. 4,530,833 (Wilkins et al.) (1985); U.S. Pat. No. 4,533,630 (Wilkins et al.) (1985); and U.S. Pat. No. 4,879,218 (Wilkins et al.) (1989)). There are significant difficulties in producing sufficient quantities of the *C. difficile* toxin A and toxin B proteins. These methods are generally cumbersome and expensive. However, the present invention provides for the construction and recombinant expression of a nontoxic truncated portions or fragments of *C. difficile* toxin A and toxin B in strains of *E. coli*. Such methods are more effective and commercially feasible for the production of sufficient quantities of a protein molecule for raising humoral immunogenicity to antigens.

Part of the difficulty that the present invention overcomes concerns the fact that large proteins are difficult to express at high levels in *E. coli*. Further, an unusually high content of AT in these clostridial gene sequences (i.e., AT-rich) makes them particularly difficult to express at high levels (Makoff et al. *Bio/Technology* 7:1043–1046 (1989)). It has been reported that expression difficulties are often encountered when large (i.e., greater than 100 kd) fragments are expressed in *E. coli*. A number of expression constructs containing smaller fragments of the toxin A gene have been constructed, to determine if small regions of the gene can be expressed to high levels without extensive protein degradation. In all cases, it was reported that higher levels of intact, full length fusion proteins were observed rather than the larger recombinant fragments (Kink et al., U.S. Pat. No. 5,736,139; see: Example 11(c)). It has been further reported that AT-rich genes contain rare codons that are thought to interfere with their high-level expression in *E. coli* (Makoff et al. *Nucleic Acids Research* 17:10191–10202). The present invention provides for methods to produce genes that are both large and AT-rich and immunogenic compositions thereof. For example, the toxin A repeating units are approximately 98 kDa and the gene sequence has an AT content of approximately 70% that is far above the approximately 50% AT content of the *E. coli* geneome. The present invention provides for methods of expressing AT-rich genes (including very large ones) at high levels in *E. coli* without changing the rare codons or supplying rare tRNA.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are incorporated in their entirety by reference herein. Specifically, the present application claims benefit of priority to U.S. provisional patent application serial No. 60/190,111, which was filed on Mar. 20, 2000; and U.S. provisional patent application serial No. 60/186,201, which was filed on Mar. 1, 2000; and U.S. provisional patent application serial No. 60/128,686, which was filed on Apr. 9, 1999, and which provisional patent applications are incorporated in their entirety by reference herein.

SUMMARY OF THE INVENTION

The present invention is drawn to an immunogenic composition that includes recombinant proteins. The genes encoding the proteins are isolated from a strain of *C. difficile*. A preferred embodiment of this invention provides that at least one protein is a toxin or a toxin fragment. A further preferred embodiment provides that the toxin is *C. difficile* toxin A or toxin B. A more preferred embodiment of the present invention provides that the recombinant protein components are nontoxic and comprise a portion of both toxins including all of the amino acid sequence of the *C. difficile* toxin A or toxin B repeating units (RARU or rBRU) or fragment thereof. The immunogenic composition may further include a carbohydrate moiety as well as a pharmaceutically acceptable carrier or other compositions in a formulation suitable for injection in a mammal.

Another embodiment of the invention is that the rARU and rBRU components are combined, preferably in a manner that results in high levels of neutralizing antibodies to toxins A and B when the immunogenic composition is used in vaccine. The components may be admixed at different ratios. Further, the rARU and rBRU components may be chemically or physically linked to form a complex. Another preferred embodiment is that the rARU and rBRU sequences, or fragments thereof, may be genetically fused in a manner that results in the production of a hybrid molecule. A further embodiment is that the immunogenic composition elicits antibodies that precipitate the native *C. difficile* toxins and neutralize their cytotoxic activity thus providing protection against *C. difficile* associated disease.

BRIEF DESCRIPTION OF THE DRAWINGS

FIG. 1. Schematic of toxins A and B. The repeating units of the toxins function in binding to the cell surface. Antibodies to the repeating units of the toxins neutralize FIG. 2 shows the nucleotide sequence (SEQ ID NO: 1) (numbers 5690–8293, GenBank accession number M30307, Dove et al. 1993) of the toxin A gene region that encodes rARU and the toxin A stop codon. The sequence encodes for the entire repeating units of toxin A from *C. difficile* strain VPI 10463 as defined by Dove et al. (Dove et al., *Infect Immun.* 58:480–488 (1990)). In addition it encodes for 4 amino acids upstream of the beginning of the repeating units and a small stretch of hydrophobic amino acids at the end of toxin A. The Sau3A site (underlined) at the beginning of the sequence was used to subclone the gene fragment to an expression vector. The stop codon at the end of the sequence is italicized.

FIG. 3 shows the amino acid sequence (SEQ ID NO:2) (GenBank accession number M303307) of rARU. The invention contemplates the use of any recombinant protein containing this amino acid sequence, any fragment therein, any fusion protein containing rARU or a fragment therein, and any larger fragment from toxin A carrying all or part of rARU, as a carrier for conjugate vaccine compositions.

HindIII/EcoRI sites were eliminated by blunt ending.

Figure 4:
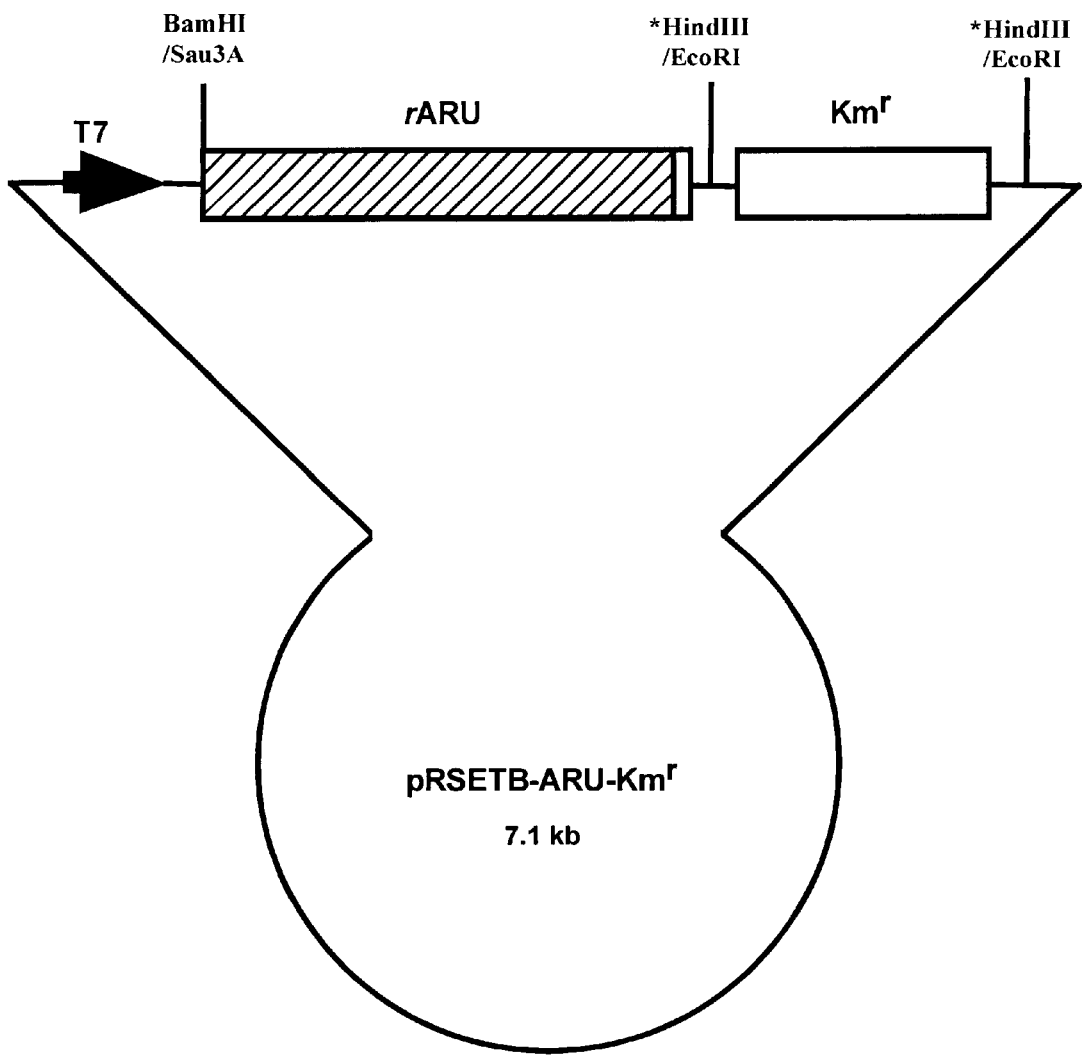
FIG. 4 shows the expression vector pRSETB-ARU-Km$^r$ used for expression of rARU. A Sau3A/HindIII gene fragment of approximately 2.7 kb containing the entire nucleotide sequence encoding rARU, stop codon, and a small region downstream of the toxin A stop codon, was subcloned to the vector pRSETB digested with BarrHI and HindIII. In a subsequent step the kanamycin resistance gene was subcloned at the HindIII site located downstream of the rARU gene fragment. The 1.2 kb fragment encoding the Km$^r$ gene was derived from pUC4K (GenBank accession number X06404) by digestion with EcoRI and subcloned at the HindIII site after blunt ending of the vector and Km$^r$ cassette with Klenow fragment. Expression vector pRSETB-ARU-Km$^r$ was transformed into BL21(DE3) for expression of rARU under control of the T7 promoter.
Figure 5:
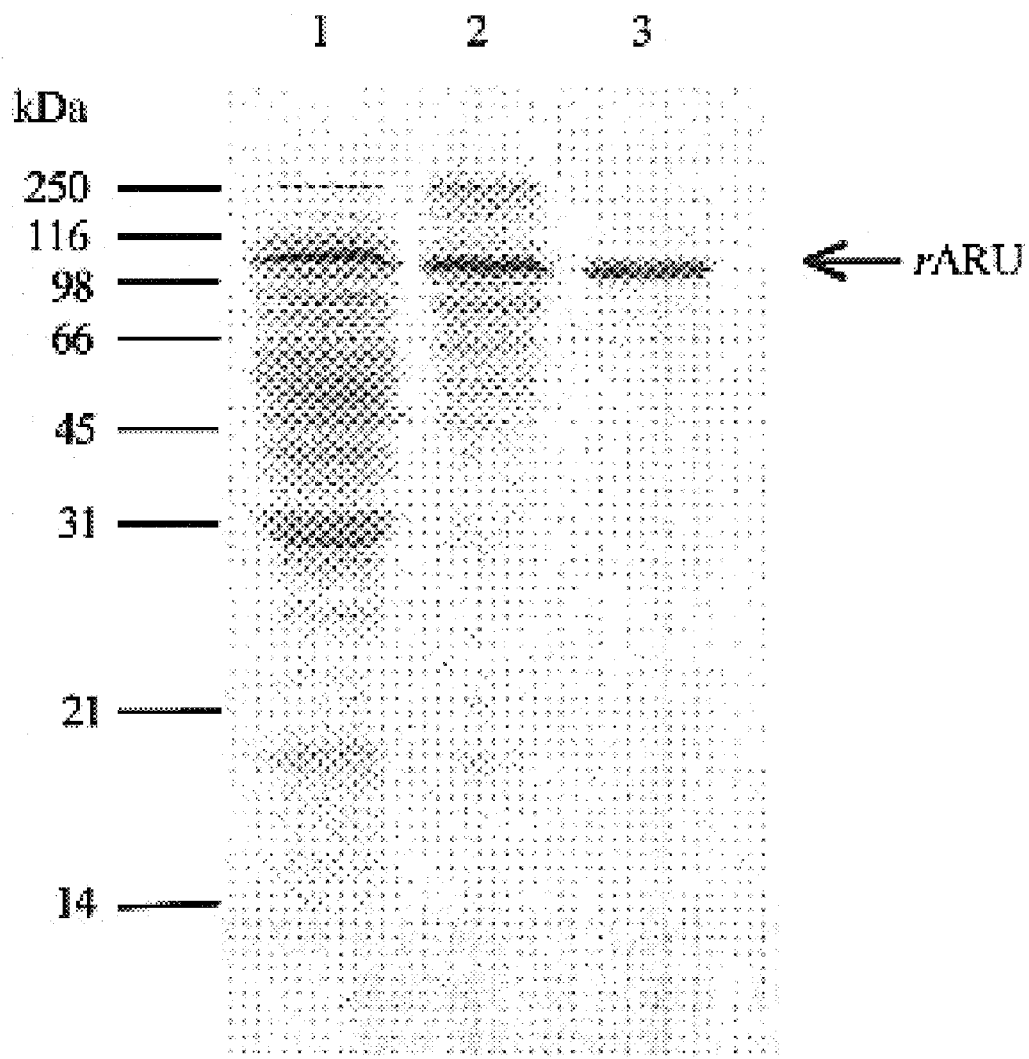

FIG. 5 shows an SDS-PAGE gel (15% acrylamide) of rARU expression and purification steps. Lanes: 1) 4 μl of 10X BL21(DE3) *E. coli*/pRSETB-ARU-Km$^r$ lysate 2) 4 μl of dialyzed 40% ammonium sulfate fraction at 10X relative to the original culture volume 3) 5 μl rARU (0.88 mg/ml) purified by CL-6B Sepharose anion exchange chromatography.

FIG. 6 shows the nucleotide sequence (SEQ ID NO:3) (GenBank accession number X531138, Wilkins et al. 1990) of the toxin B gene region that encodes rBRU and a small portion upstream. The Sau3a restriction sites used for subcloning are underlined. The sequence of the repeating units of toxin B from *C. difficile* strain VPI was defined previously (Eichel-Streiber et al. *Mol. Gen. Gen.* 233:260–268).

FIG. 7 shows the amino acid sequence (SEQ ID NO:4) (GenBank accession number X53138) of rBRU and a small upstream region. The invention contemplates the use of any recombinant protein containing this amino acid sequence, any fragment therein, any fusion protein containing rBRU or a fragment therein, and any larger fragment from toxin B carrying all or part of rBRU, as a component in a vaccine against *C. difficile*.

Figure 8:
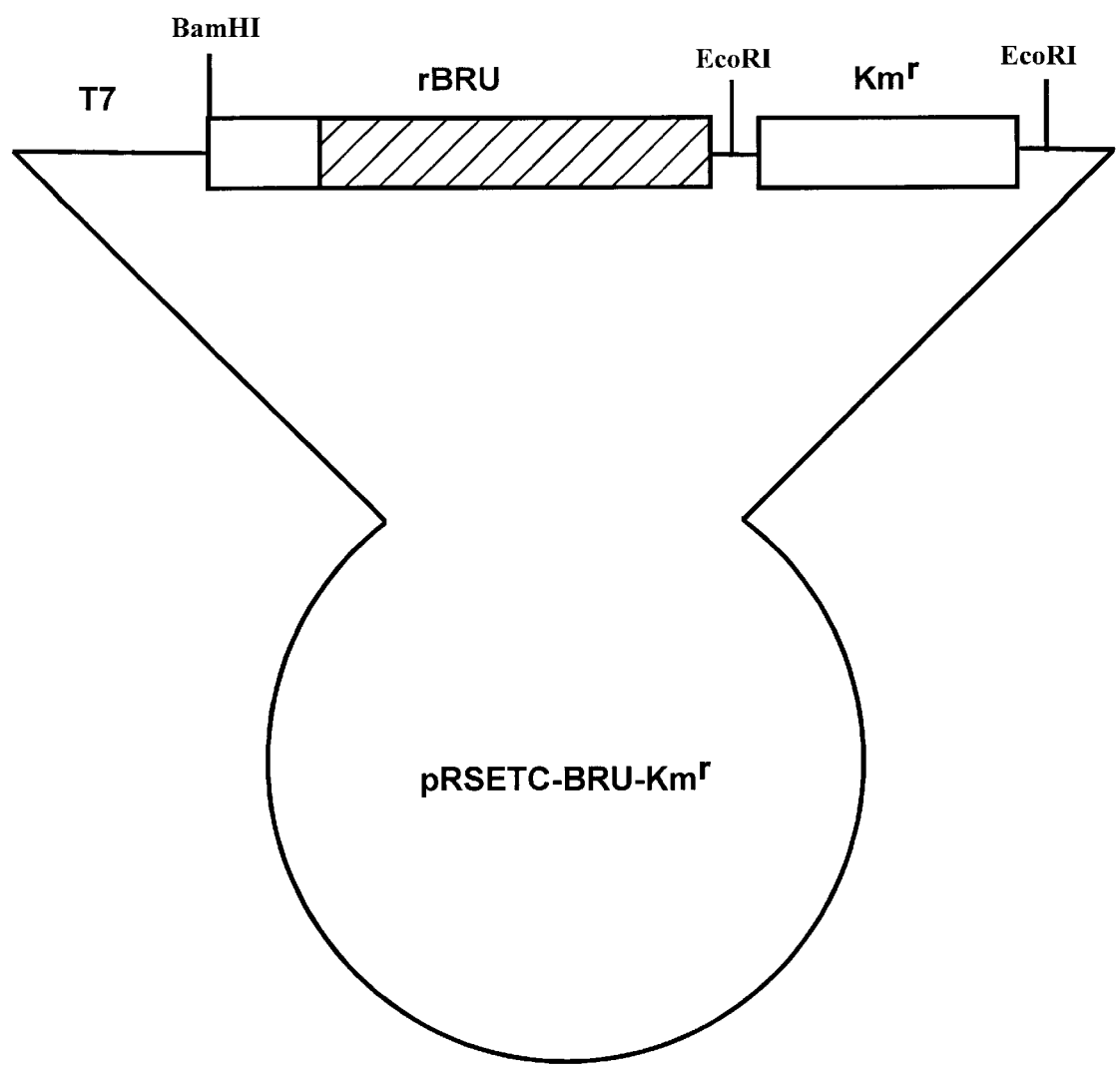

FIG. 8 shows the expression vector pRSETC-BRU-Km$^r$ used for expression of rBRU. A gene fragment of approximately 1.8 kb containing nearly the entire nucleotide sequence encoding rBRU (final 10 amino acids of toxin B are eliminated) was subcloned from the toxin B gene (Phelps et al. *Infect. Immun.* 59:150–153 (1991)) to pGEX-3X. A BamHI/EcoRI from pGEX-3X-BRU was subcloned to pRSETC. In a subsequent step the kanamycin resistance gene was subcloned at the EcoRI site located downstream of the rBRU gene fragment. The 1.2 kb fragment encoding the Km$^r$ gene was derived from pUC4K (GenBank accession number X06404) by digestion with EcoRI. Expression vector pRSETC-BRU-Km$^r$ was transformed into BL21 (DE3) for expression of rBRU under control of the T7 promoter.

Figure 9:
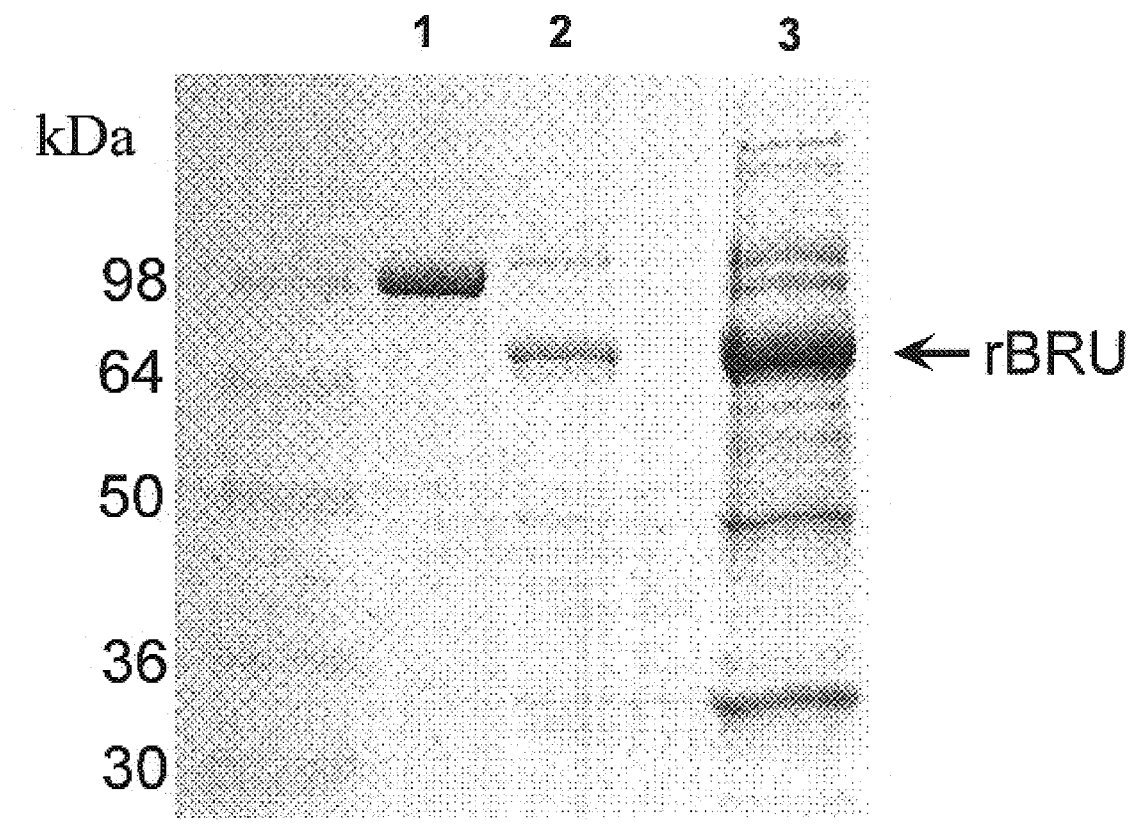

FIG. 9. SDS-PAGE of purified rARU and partially purified rBRU. Lanes; 1) rARU purified by sequential ammonium sulfate precipitation and Sepharose CL-6B anion exchange chromatography, 2) rBRU partially purified by ammonium sulfate precipitation and hydrophobic interaction chromatography on phenyl Sepharose, 3) lysate (10X concentration) of *Escherichia coli* BL21(DE3)/pRSETC-BRU-Km$^r$.

Figure 10:
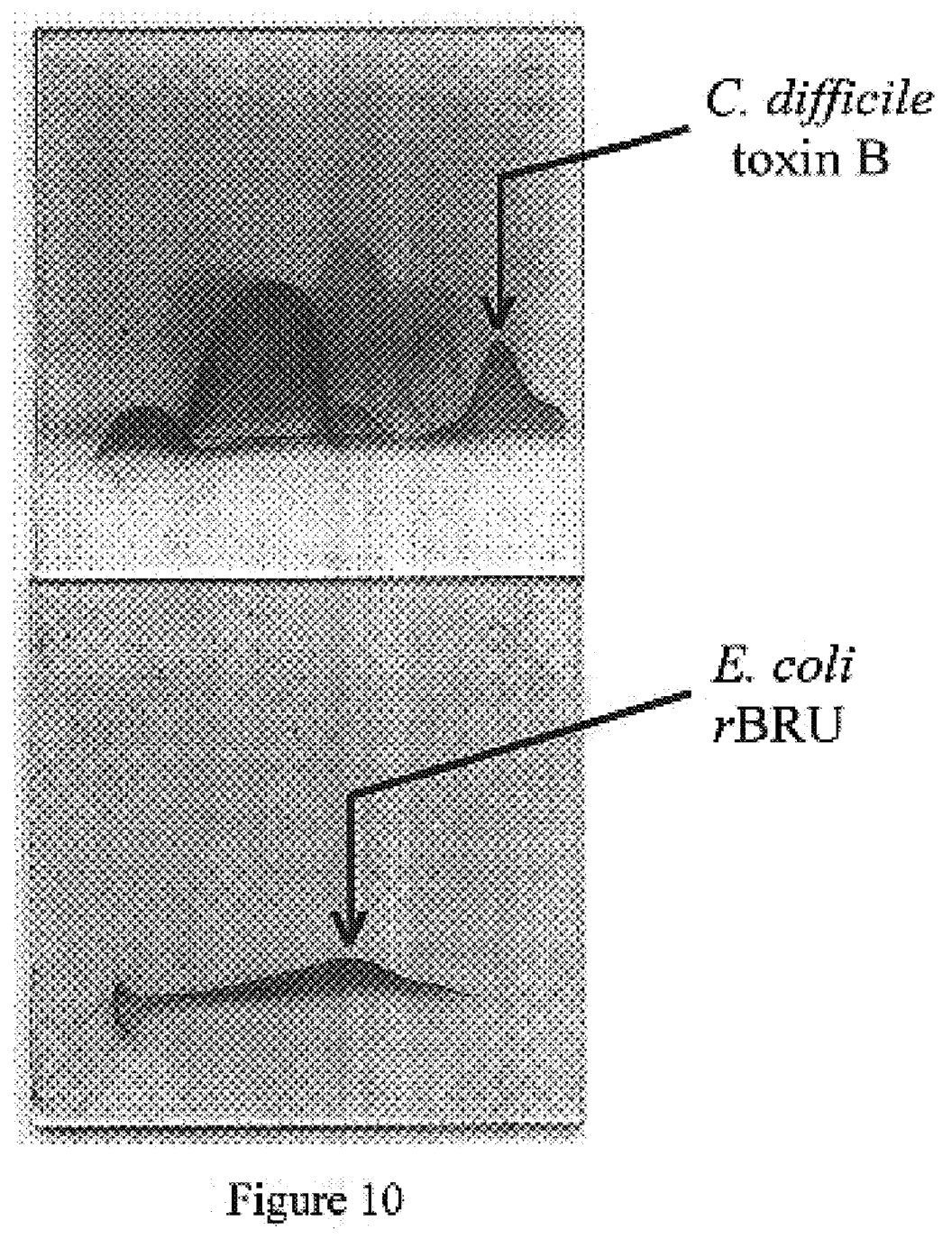

FIG. 10. Crossed-immunoelectrophoresis of (A) *C. difficile* culture filtrate and (B) partially purified rBRU. *C. difficile* goat antisera was used as the precipitating antibody.

Figure 11:
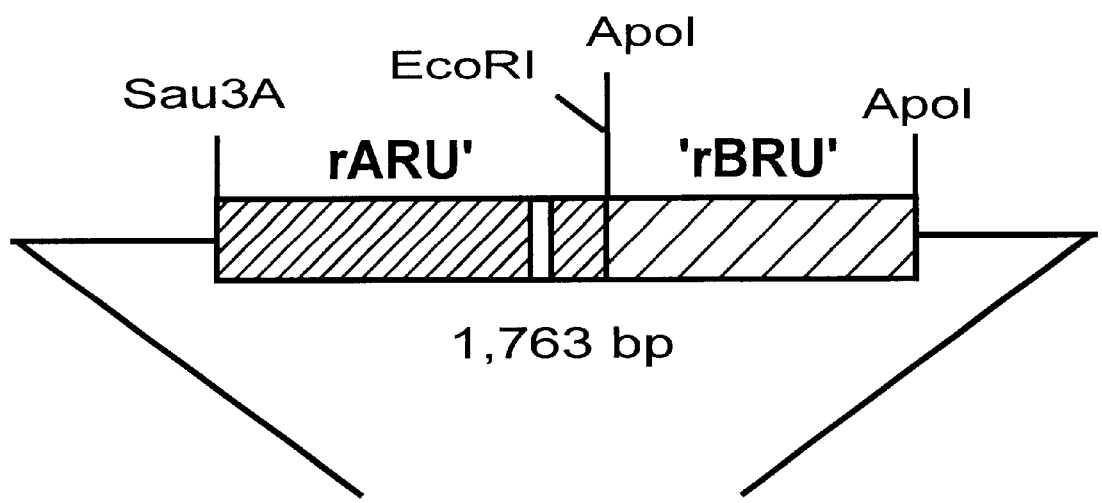

FIG. 11. shows an example of a genetic fusion of rARU and rBRU. A Sau3A/EcoRI toxin A gene fragment (nucleotides 5530 through 6577) may be fused to an ApoI toxin B gene fragment (nucleotides 5464 through 6180) to create an in-frame 1,763 bp gene fusion expressing a 588 amino acid rARU'/'rBRU' fusion protein of approximately 68 kDa containing a significant portion of the repeating units from both toxin genes. The rARU' fragment encodes an epitope for PCG-4 represented by the open bar in the rARU' portion of the gene fusion.

DETAILED DESCRIPTION OF THE INVENTION

The present invention is drawn to an immunogenic composition that includes at least one-recombinant protein component, wherein the gene encoding the protein component is isolated from a strain of *Clostridium difficile*. A preferred embodiment of this invention provides that the protein is a toxin or a toxin fragment. An even further preferred embodiment provides that the toxin is toxin A, with yet a further preferred embodiment being a portion of the toxin containing all of the amino acid sequence of the toxin A repeating units (rARU) or fragment thereof. Another preferred embodiment is that the toxin is toxin B, with yet another preferred embodiment being a portion of the toxin containing all of the amino acid sequence of the repeating units (rBRU) or a fragment thereof. The immunogenic composition may further include a pharmaceutically acceptable carrier or other compositions in a formulation suitable for injection in a mammal.

These immunogenic compositions of the present invention elicit an immune response in a mammalian host, including humans and other animals. The immune response may be either a cellular dependent response or an antibody dependent response or both and further the response may provide immunological memory or a booster effect or both in the mammalian host. These immunogenic compositions are useful as vaccines and may provide a protective response by the mammalian subject or host to infection by strains of *Clostridium difficile*.

The present invention further includes methods for producing an immunogenic composition by: constructing a genetic sequence encoding a recombinant protein component, where the gene encoding the protein component is isolated from a strain of *Clostridium difficile*, expressing the recombinant protein component in a microbial host; recovering the recombinant protein from a culture of the host; conjugating the protein to a second protein component, and recovering the conjugated protein and polysaccharide component. The protein component may also consist of a fusion protein, whereby a portion of said recombinant protein is genetically fused to a second protein component. Preferably the expression of the genetic sequence is regulated by an inducible promoter that is operatively positioned upstream of the sequence and is functional in the host. Even further, said genetic sequence is maintained throughout the growth of the host by constant and stable selective pressure. Maintenance of the expression vector may be conferred by incorporation in the expression vector of a genetic sequence that encodes a selective genotype, the expression of which in the microbial host cell results in a selective phenotype. Such selective genotypes, include a gene encoding resistance to antibiotics, such as kanamycin. The expression of this selective genotypic sequence on the expression vector in the presence of a selective agent or condition, such as the presence of kanamycin, results in stable maintenance of the vector throughout growth of the host. A selective genotype sequence could also include a gene complementing a conditional lethal mutation.

Other genetic sequences may be incorporated in the expression vector, such as other drug resistance genes or genes that complement lethal mutations.

Microbial hosts of this invention may include: Gram positive bacteria; Gram negative bacteria, preferably *E. coli*; yeasts; filamentous fungi; mammalian cells; insect cells; or plant cells.

The methods of the present invention also provide for a level of expression of the recombinant protein in the host at a level greater than about 10 mg/liter of the culture, more preferably greater than about 50 mg/liter and even more preferably at 100 mg/liter or greater than about 100 mg/liter. The molecular weight of the protein is greater than about 30 kDa, preferably greater than about 50 kDa and even more preferably greater than about 90 kDa. This invention also provides that the protein may be recovered by any number of methods known to those in the art for the isolation and recovery of proteins, but preferably the recovery is by ammonium sulfate precipitation followed by ion exchange chromatography.

The present invention further includes methods for preparing the immunogenic composition that provides that the protein component is conjugated to a second protein component by one of a number of means known to those in the art, particularly an amidization reaction.

Also, high yields of recombinant protein may be dependent on the growth conditions, the rate of expression, and the length of time used to express AT-rich gene sequences. In general, AT-rich genes appear to be expressed at a higher level in *E. coli* during a post-exponential or slowed phase of growth. High-level production of the encoded protein requires moderate levels of expression over an extended period (e.g. 20–24 h) of post-exponential growth rather than the typical approach of high-level expression during exponential growth for shorter periods (e.g. 4–6 h). In this regard, it is more efficient to maintain plasmids carrying the gene of interest by maintaining constant selective pressure for the gene or its expression vector during the extended period of growth. One aspect of the present invention is using an antibiotic that is not inactivated or degraded during growth of the expression host cell as is found with ampicillin. One such preferred embodiment involves the expression of genes encoding resistance to kanamycin as the selective phenotype for maintaining the expression vector which comprises such kanamycin resistance genetic sequences. Expression of large AT-rich clostridial genes in *E. coli* at levels (>100 mg/liter) provided for by methods of the present invention was hitherto unknown.

Terms as used herein are based upon their art recognized meaning and should be clearly understood by the ordinary skilled artisan.

An immunogenic composition is any composition of material that elicits an immune response in a mammalian host when the immunogenic composition is injected or otherwise introduced. The immune response may be humoral, cellular, or both.

A fusion protein is a recombinant protein encoded by a gene or fragment of a gene, genetically fused to another gene or fragment of a gene.

A booster effect refers to an increased immune response to an immunogenic composition upon subsequent exposure of the mammalian host to the same immunogenic composition. A humoral response results in the production of antibodies by the mammalian host upon exposure to the immunogenic composition.

rARU is a recombinant protein containing the repeating units of *Clostridium difficile* toxin A as defined by Dove et al. (Dove et al. *Infect. Immun.* 58:480–488 (1990)). The nucleotide sequence encoding rARU and the amino acid sequence of rARU are shown in FIGS. 2 and 3, respectively. The rARU expressed by pRSETB-ARU-Km$^r$ contains the entire repeating units region of toxin A. The invention further contemplates the use of this recombinant protein component, or any other protein component containing the entire repeating units of toxin A or any fragment therein, whether expressed alone or as a fusion protein.

Similar methods may be used to isolate, clone and express a recombinant protein component comprising the repeating units of *Clostridium difficile* toxin B (rBRU). The nucleotide sequence encoding rBRU and the amino acid sequence of rBRU are shown in FIGS. 6 and 7, respectively. The rBRU expressed by pRSETC-BRU-Km$^r$ contains the entire repeating units region of toxin B (see FIG. 8).

The present methods provide for preparation of immunogenic compositions comprising rARU or rBRU or both, which are useful as vaccines. Immunogenic compositions may be formulated as vaccines in a pharmaceutically acceptable carrier or diluent (e.g., water, a saline solution (e.g., phosphate-buffered saline), a bicarbonate solution (e.g., 0.24 M NaHCO.sub.3), a suppository, cream, or jelly), which are selected on the basis of the mode and route of administration, and standard pharmaceutical practice, see: U.S. Pat. No. 5,919,463 Thomas, et al., (1999), which is incorporated in its entirety by reference herein. Suitable pharmaceutical carriers and diluents, as well as pharmaceutical necessities for their use in pharmaceutical formulations, are described in Remington's Pharmaceutical Sciences (Alfonso Gennaro et al., eds., 17th edn., Mack Publishing Co., Easton Pa., 1985), a standard reference text in this field, in the USP/NF, and by Lachman et al. (The Theory & Practice of Industrial Pharmacy, 2nd edn., Lea & Febiger, Philadelphia Pa., 1976). In the case of rectal and vaginal administration, the vaccines are administered using methods and carriers standardly used in administering pharmaceutical materials to these regions. For example, suppositories, creams (e.g., cocoa butter), or jellies, as well as standard vaginal applicators, droppers, syringes, or enemas may be used, as determined to be appropriate by one skilled in the art.

The vaccine compositions of the invention may be administered by any route clinically indicated, such as by application to the surface of mucosal membranes (including: intranasal, oral, ocular, gastrointestinal, rectal, vaginal, or genito-urinary). Alternatively, parenteral (e.g., intravenous, subcutaneous, intraperitoneal, or intramuscular) modes of administration may also be used. The amounts of vaccine administered depend on the particular vaccine antigen and any adjuvant employed; the mode and frequency of administration; and the desired effect (e.g., protection and/or treatment), as determined by one skilled in the art. In general, the vaccines of the invention will be administered in amounts ranging between 1 µg and 100 mg. Administration is repeated as is determined to be necessary by one skilled in the art. For example, a priming dose may be followed by 3 booster doses at weekly intervals.

Having now generally described the invention, the same will be more readily understood through reference to the following examples which are provided by way of illustration, and are not intended to be limiting of the present invention, unless specified.

EXAMPLES

Example 1

Construction of rARU Expression Vector.

The vector pRSETB-ARU-Km$^r$ used for expression and purification was constructed using standard techniques for cloning (Sambrook et al., *Molecular Cloning: A Laboratory Manual* (1989)). The nucleotide sequence of the toxin A gene fragment encoding rARU was derived from the cloned toxin A gene (Dove et al., *Infect. Immun.* 58:480–488 (1990); Phelps et al., *Infect Immun.* 59:150–153 (1991)) and is shown in FIG. 2. The gene fragment encodes a protein 867 amino acids in length (FIG. 3) with a calculated molecular weight of 98 kDa. The gene fragment was subcloned to the expression vector pRSETB. A kanamycin resistance gene was subsequently subcloned to the vector. The resulting vector pRSETB-ARU-Km$^r$ expresses rARU. An additional 31 amino acids at the N-terminus of the recombinant protein are contributed by the expression vector pRSETB. The final calculated molecular weight of the recombinant protein is 102 kDa.

Example 2

Expression and Purification of rARU.

*Escherichia coli* T7 expression host strain BL21 (DE3) was transformed with pRSETB-ARU-Km$^r$ as described (Sambrook et al. *Molecular Cloning: A Laboratory Manual* (1989)). One liter cultures were inoculated with 10 ml of overnight growth of Escherichia coli BL21(DE3) containing pRSETB-ARU-Km$^r$ and grown at 37° C. in Terrific broth (Sigma, St. Louis, Mo.) containing 25 µg/ml of kanamycin to an O.D. 600 of 1.8–2.0 and isopropyl B-D-thiogalactopyranoside (IPTG) was added to a final concentration of 40 µM. Cells were harvested after 22 h of induction, suspended in 0.1 liter of standard phosphate buffered saline, pH 7.4, containing 0.2% casanino acids, and disrupted by sonication. Cellular debris was removed from the lysate by centrifugation. Lysates typically contained a titer (reciprocal of the highest dilution with an A$_{450}$ greater than 0.2) of $10^6$ in the TOX-A test EIA (TechLab, Inc., Blacksburg, Va.). Lysates were saturated with 40% ammonium sulfate, stirred at 4° C. overnight and precipitating proteins were harvested by centrifugation. The ammonium sulfate fraction was suspended in 0.1 liters of 5 mM $K_2PO_4$, 0.1 M $NaCl_2$, pH 8.0 and dialyzed extensively against the same buffer at 4° C. Insoluble material was removed by centrifugation. The dialyzed solution was passed through a column containing Sepharose CL-6B chromatography media (50 ml media/100 ml solution). Fractions were collected and monitored for the presence of rARU by EIA using the TOX-A test. Fractions containing EIA activity were analyzed by SDS-PAGE for the presence of rARU at a molecular weight of approximately 102 kDa. Fractions containing a single band of rARU were pooled. To further ensure purity the pooled solution was again passed over a Sepharose CL-6B column (25 ml media/100 ml protein solution). The solution containing purified rARU was filtered sterilized by passage through a 22 $\mu$ filter and stored at 4° C. Purified rARU along with samples from the steps of purification (lysate and dialyzed ammonium sulfate fraction) are shown in FIG. 5. The procedure typically yields approximately 100 mg rARU per liter of *E. coli*/pRSETB-ARU-$Km^r$ culture. A combined 6-liter batch yielded 0.850 liters of rARU at 0.88 mg/ml for a total of 748 mg of rARU or 125 mg/liter of culture. The amount of rARU recovered represented 23% of the total soluble protein.

Example 3

Construction of rBRU Expression Vector.

The vector pRSETC-BRU-$Km^r$ used for expression and purification was constructed using standard techniques for cloning (Sambrook et al., *Molecular Cloning: A Laboratory Manual* (1989)). The nucleotide sequence of the toxin B gene fragment encoding rBRU was derived from the cloned toxin B gene (Barroso et al., *Nucleic Acids Res* 18:4004 (1990)) and is shown in FIG. 6. The gene fragment encodes a protein 622 amino acids in length with a molecular weight of approximately 70 kDa. The gene fragment was subcloned to the expression vector pRSETC. A kanamycin resistance gene was subsequently subcloned to the vector. The resulting vector pRSETC-BRU-$Km^r$ expresses rBRU.

Example 4

High-level Expression and Partial Purification of rBRU.

One liter of *Escherichia coli* pRSETC-BRU-$Km^r$ was grown for 25 h at 37° C. in a shaking incubator. Cells were harvested by centrifugation and resuspended in 0.1 liter phosphate buffered saline with 0.2% casamino acids. Supernatant of the culture at harvest had a pH of 6.2. Cells were disrupted by sonication and cellular debri was removed by centrifugation. The 10X lysate is shown in FIG. 9, lane 3.

Example 5

Immune Response to the rARU Component of the Conjugates.

Antibodies to *C. difficile* toxin A (CDTA). Antibodies to native toxin A were measured by ELISA, with toxin A isolated from *C. difficile* as the coating antigen, and by in-vitro neutralization of cytotoxicity (Lyerly et al. *Infect. Immun*. 35:1147–1150 (1982)). Human intestinal epithelial HT-29 cells (ATCC HTB 38) were maintained in 96 well plates with McCoy's 5A medium supplemented with 10% fetal calf serum in a 5% $CO_2$ atmosphere. HT-29 cells were chosen because of their high sensitivity to CDTA probably because of the high density of the carbohydrate receptor on their surface. Serial 2-fold dilutions of sera were incubated with 0.4 $\mu$g/ml of CDTA for 30 min at room temperature. CDTA-serum mixtures were added to the wells at a final concentration of 20 ng of toxin A per well (about 200 times the minimal cytotoxic dose for HT-29 cells) in a final volume of 0.2 ml. The neutralization titer is expressed as the reciprocal of the highest dilution that completely neutralized cytotoxicity.

TABLE 1

Serum antibodies ($\mu$g/ml) to *Clostridium difficile* toxin A (CDTA) elicited in mice by recombinant enterotoxin A (rARU) or polysaccharides bound to rARU alone or succinylated (rARUsucc)

| Conjugate | $\mu$g rARU Injected | ELISA (Geometric mean and 25–75 centiles) First injection | Second injection | Third injection |
|---|---|---|---|---|
| rARU* | 6.94 | ND | ND | 717 (621–863) |
| Pn14-rARU | 1.29 | 3.70 (2.55–5.08) | 80.1 (69.8–131) | 194 (113–236) |
| Pn14rARU succ | 7.30 | 7.94 (5.21–11.3) | 183 (146–175) | 371 (274–463) |
| SF-rARU | 3.90 | ND | 433 (258–609) | 613 (485–778) |
| SF-rARUsucc | 6.94 | ND | 191 (118–291) | 518 (366–615) |
| SF-rARU* | 3.90 | ND | ND | 437 (372–547) |
| SF-rARUsucc* | 6.94 | ND | ND | 242 (172–443) |
| K1 | 8.08 | 10.7 (6.75–17.2) | 84.9 (72.5–131) | 390 (279–470) |

183 vs 7.94 p = 0.0001, 3.71 vs 183 p = 0.0005, 80.1 vs 3.70 p = 0.0001, 194 vs 80.1 p = 0.007, 7.94 vs 3.70 p = 0.01, 183 vs 80.1 p = 0.004, 371 vs 194 p = 0.01

*hsd/ICR mice. Remainder were NIH SA mice. ND (not done).

6 wks-old mice were injected SC with 2.5 $\mu$g of polysaccharide as a conjugate at 2 wk intervals. Groups of mice (n = 10) were exsanguinated 7 days after each injection and their sera assayed for anti-CDTA by ELISA.

All 5 conjugates elicited high levels of anti-CDTA (194–613 $\mu$g/ml) (Table 1). Since the 2.5 $\mu$g immunizing dose of the conjugates was based on its polysaccharide content, the amount of rARU injected was different for each conjugate. For example, on a protein weight basis, Pn14-rARU, with 1.29 $\mu$g of rARU, elicited 194 $\mu$g CDTA antibody/ml (150.3 $\mu$g Ab/$\mu$g rARU injected). In contrast, Pn14-rARUsucc, that contained 7.3 $\mu$g of rARU per dose, elicited 371 $\mu$g CDTA antibody/ml (50.8 $\mu$g Ab/$\mu$g rARUsucc injected). Pn14-rARU induced more anti-CDTA per $\mu$g rARU than Pn14-rARUsucc, however, the total amount of anti-CDTA elicited by Pn14-rARUsucc was greater due to its higher content of rARU. The difference between the levels of anti-CDTA elicited by Pn14-rARU (194 $\mu$g CDTA antibody/ml) compared with Pn14-rARUsucc (371 $\mu$g CDTA antibody/ml) was significant.

SF-rARU, containing 3.9 $\mu$g of rARU, elicited 437 $\mu$g CDTA antibody/ml (112.0 $\mu$g Ab/$\mu$g rARU injected) compared to 518 $\mu$g CDTA antibody/ml for SF-rARUsucc (34.9 $\mu$g Ab/$\mu$g rARUsucc injected). Although the specific immunogenic activity for the rARUsucc was lower than that of the rARU in the SF conjugates, there was no statistical difference between the levels of CDTA antibody elicited by the two conjugates (437 $\mu$g Ab/ml for SF-rARUsucc vs 242 $\mu$g Ab/ml for SF-rARU).

K1-rARUsucc, that elicited 390 $\mu$g CDTA antibody/ml, had comparable specific immunogenic activity of its rARU component (48 $\mu$g Ab/ml per $\mu$g rARUsucc).

Example 6

CDTA Neutralizing Antibodies.

Individual sera obtained 7 days after the third injection of the conjugates were assayed individually for their neutralization of approximately 200 times the cytotoxic dose of CDTA on human intestinal epithelial HT-29 cells. All sera from the mice immunized with the conjugates had a neutralizing titer greater than or equal to 64. The geometric mean and range of neutralizing titers for each conjugate is shown in Table 2.

TABLE 2

Serum neutralizing activity against the in vitro cytotocicity for HT-29 cells of *Clostridium difficile* toxin A (CDTA)

| Immunogen | μg Ab/ml (ELISA) | | Reciprocol neutra;ization titer (GM and range) |
|---|---|---|---|
| Pn14-rARU | 194 | 104 | 64–256 |
| Pn14-rARUsucc | 371 | 111 | 64–128 |
| SF-rARU | 613 | 194 | 64–256 |

Neutralizing titers were the highest serum dilution that completely inhibited the cytotoxicity of CDTA (20 ng/well) on HT-29 cells. The titers represent the geometric mean of sera from general purpose Swiss Albino mice (n = 10) obtained 7 days after the 3rd injection. Anti-CDTA was measured by ELISA and the mean value expressed as μg Ab/ml serum.
*Affinity purified goat antibody Example 7

Protection Against Lethal Challenge with CDTA (Table 3).

Hsd/ICR mice were injected with SF-rARU, SF-rARUsucc or rARU as described in EXAMPLE 4 above. One week after the third injection, the mice were challenged intraperitoneally with a lethal dose (150 ng) of CDTA. Almost all mice vaccinated with either conjugate or rARU were protected. Based upon the amount of rARU injected, rARU and SF-rARU elicited similar levels of anti-CDTA. As expected, SF-rARUsucc elicited lower levels of anti-CDTA than the other two immunogens but the recipients were comparably protected.

Conjugate-induced antibody levels approached or surpassed the neutralizing activity of an affinity-purified goat antibody, containing 0.5 mg/ml, that was raised against formalin inactivated CDTA.

TABLE 3

Protection of mice against lethal challenge with 150 ng of *Clostridium difficile* toxin A (CDTA)[a] induced by vaccination with polysaccharide-rARU conjugates

| Immunogen | μg rARU injected | Survivals/ total | CDTA antibodies (ELISA)[b] | Reciprocal neutralization titer[c] |
|---|---|---|---|---|
| rARU | 6.94 | 19/20 | 717 (621–863) | 128–256 |
| SF-rARU | 3.90 | 17/20 | 437 (372–547) | 128–256 |
| SF-rARUsucc | 6.94 | 19/20 | 242 (172–443) | 64–256 |
| PBS | 0 | 2/15 | Not determined | <2 |

[a]Mice (hsd/ICR) injected I.P. with 150 ng of CDTA 7 days after the 3rd injection of rARU or conjugate.
[b]Mean antibody level (25–75 centiles) of sera used for pool (n = 10 from each group bled 4 h before challenge with CDTA.
[c]Highest dilutions of sera (range) that completely neutralized the cytotoxicity of CDTA (20 ng/well) on HT-29 cells.

This invention has been described by a direct description and by examples. As noted above, the examples are meant to be only examples and not to limit the invention in any meaningful way. Additionally, one having ordinary skill in the art to which this invention pertains in reviewing the specification and claims which follow would appreciate that there are equivalents to those claimed aspects of the invention. The inventors intend to encompass those equivalents within the reasonable scope of the claimed invention.

LITERATURE CITED

U.S. Pat. No. 5,098,826 (Wilkins et al.) (1992).
U.S. Pat. No. 5,736,139 (Kink et al.) (1998)
U.S. Pat. No. 5,919,463 (Thomas et al.) (1999)
Lyerly, D. M. and T. D. Wilkins, in *Infections of the Gastrointestinal Tract*, Chapter 58,
pages 867–891, Raven Press, Ltd, New York 1995
Moncrief et al., *Infect. Immun.* 65:1105–1108 (1997);
Barroso et al., *Nucl. Acids Res.* 18:4004 (1990);
Dove et al. *Infect. Immun.* 58:480–488 (1990)). (
Krivan et al., *Infect. Immun.* 53:573–581 (1986);
Tucker, K. and T. D. Wilkins, *Infect. Immun.* 59:73–78 (1991)).
Just et al. *Nature* 375:500–503 (1995),
Just et al. *J. Biol. Chem* 270:13932–13939 (1995)).
Hofmann et al. *J. Biol. Chem.* 272:11074–11078 (1997),
Faust and Song, *Biochem. Biophys. Res. Commun.* 251:100–105 (1998))
Lyerly et al. *Current Microbiology* 21:29–32 (1990)

What is claimed is:

1. A composition comprising a recombinant protein component, wherein said protein component comprises the repeating unit portion of *C. difficile* toxin A (rARU) in admixture with a pharmaceutically acceptable carrier, and wherein said composition elicits the production of neutralizing antibodies with respect to toxin A.

2. The composition of claim 1, wherein said protein component is a fusion protein.

3. The composition of claim 1 that elicits a protective response in a mammalian host against *C. difficile*.

4. The composition of claim 1, wherein said protein component comprises both rARU and rBRU in admixture with a pharmaceutically acceptable carrier, and wherein said composition elicits the production of neutralizing antibodies with respect to toxin A and toxin B.

5. The composition of claim 4, wherein the protein component is a fusion protein.

6. The composition of claim 4 that elicits a protective response in a mammalian host against *C. difficile*.

7. A composition comprising a recombinant protein component, wherein said protein component comprises the repeating unit portion of *C. difficile* toxin B (rBRU) in admixture with a pharmaceutically acceptable carrier, and wherein said composition elicits the production of neutralizing antibodies with respect to toxin B.

8. The composition of claim 7, wherein said protein component is a fusion protein.

9. The composition of claim 7 that elicits a protective response in a mammalian host against *C. difficile*.

* * * * *